United States Patent
Neff et al.

(10) Patent No.: US 8,828,023 B2
(45) Date of Patent: Sep. 9, 2014

(54) MEDICAL WORKSTATION

(75) Inventors: Thomas Neff, Munich (DE); Dirk Jacob, Marktoberdorf (DE); Martin Kuschel, Munich (DE); Marc-Walter Ueberle, Friedberg (DE); Tobias Ortmaier, Hemmingen (DE)

(73) Assignee: KUKA Laboratories GmbH, Augsburg (DE)

( * ) Notice: Subject to any disclaimer, the term of this patent is extended or adjusted under 35 U.S.C. 154(b) by 176 days.

(21) Appl. No.: 13/288,614

(22) Filed: Nov. 3, 2011

(65) Prior Publication Data

US 2012/0116416 A1 May 10, 2012

(30) Foreign Application Priority Data

Nov. 8, 2010 (DE) .......................... 10 2010 043 584

(51) Int. Cl.
*A61B 19/00* (2006.01)

(52) U.S. Cl.
CPC ....... *A61B 19/2203* (2013.01); *A61B 2019/223* (2013.01); *A61B 19/5225* (2013.01); *A61B 2019/2284* (2013.01); *A61B 2019/2207* (2013.01); *A61B 2019/2223* (2013.01); *A61B 19/56* (2013.01); *A61B 2019/2269* (2013.01); *A61B 2019/5289* (2013.01)
USPC ....................................................... 606/130

(58) Field of Classification Search
USPC ........ 600/102, 109; 901/15, 19, 23, 28, 2, 50; 606/130
See application file for complete search history.

(56) References Cited

U.S. PATENT DOCUMENTS

| | | | | |
|---|---|---|---|---|
| 6,113,395 | A * | 9/2000 | Hon | 434/262 |
| 6,325,808 | B1 | 12/2001 | Bernard et al. | |
| 2004/0034282 | A1 | 2/2004 | Quaid, III | |
| 2004/0186347 | A1 | 9/2004 | Shose et al. | |
| 2006/0244734 | A1* | 11/2006 | Hill et al. | 345/173 |
| 2007/0293734 | A1* | 12/2007 | Coste-Maniere et al. | 600/300 |
| 2008/0269777 | A1* | 10/2008 | Appenrodt et al. | 606/130 |
| 2009/0171184 | A1 | 7/2009 | Jenkins et al. | |
| 2009/0182226 | A1* | 7/2009 | Weitzner et al. | 600/424 |
| 2010/0145521 | A1* | 6/2010 | Prisco et al. | 700/264 |
| 2010/0240989 | A1 | 9/2010 | Stoianovici et al. | |
| 2011/0022229 | A1 | 1/2011 | Jang et al. | |

FOREIGN PATENT DOCUMENTS

| | | |
|---|---|---|
| DE | 69322202 T2 | 7/1999 |
| DE | 19842239 A1 | 3/2000 |
| DE | 10108547 A1 | 10/2002 |
| DE | 102008064140 A1 | 7/2009 |
| WO | 2009/151206 A1 | 12/2009 |
| WO | 2010025943 A1 | 3/2010 |

OTHER PUBLICATIONS

German Patent Office; Office Action in German Patent Application No. 10 2010 043 584.8 dated Jun. 1, 2011; 5 pages.
European Patent Office; Search Report in European Patent Application No. 11187650.4 dated Feb. 10, 2012; 6 pages.

* cited by examiner

*Primary Examiner* — Anhtuan T Nguyen
*Assistant Examiner* — Rynae Boler
(74) *Attorney, Agent, or Firm* — Wood, Herron & Evans, LLP

(57) ABSTRACT

A medical work station for treating a living being using a medical instrument includes at least one robot arm, which has a plurality of members connected by joints, drives to move the members, and an attaching device, at least one control device coupled with the drives, which is set up to generate signals for actuating the drives, so that the attaching devices carry out movements assigned to the signals, and a display device coupled with the control device.

11 Claims, 2 Drawing Sheets

MEDICAL WORKSTATION

TECHNICAL FIELD

The invention relates to an industrial robot having at least one robot arm.

BACKGROUND

In telepresence or teleaction, robots are remote controlled over relatively great barriers. Intended commands are registered at an operating device or input console by an operator, using sensors, and are processed and transmitted to the remotely located robot. The motion of the robot may possibly be monitored via a visual feedback channel. One application of such systems is telemanipulated surgery, where for example a doctor moves, by means of his input console, a plurality of robot arms, which for example move a medical instrument, in order to thereby treat, in particular to operate on, a living being. The input console normally includes a 3-D display device, which shows currently recorded 3-D images of the area of operation. Using input means for example in the form of grips, the doctor is able to telemanipulate the robot arms, i.e., to move them, in order to thereby move the medical instrument by means of the robot arms. WO 2010/025943 A1 discloses an example of such a medical work station.

The object of the invention is to specify an improved robot-supported medical work station.

SUMMARY

The object of the invention is fulfilled by a medical work station for treating a living being by means of a medical instrument, having
- at least one robot arm, which has a plurality of members connected by means of joints, drives for moving the members, and an attaching device which is intended to be provided with the medical instrument for treating the living being,
- at least one control device coupled with the drives, which is set up to generate signals for actuating the drives, so that the attaching device executes movements assigned to the signals,
- a display device coupled with the control device, to display at least one image of the treatment area of the living being registered during the treatment of the living being, and
- an input device, by means of which an area in the image is identifiable, the control device being set up to calculate a movement of the relevant robot arm automatically in a second operating mode on the basis of the identified area and to actuate the drives of this robot arm accordingly, so that the medical instrument, by means of this robot arm, automatically treats the area of the living being that is assigned to the identified area.

Accordingly, the medical work station is set up in such a way that an area can be identified in the image depicted by means of the display device. The image comes from the area of the living being that is being treated currently, and is preferably a three-dimensional image. The control device, which actuates the drives of the robot arms, is set up to calculate, on the basis of the identified area, a movement for the robot arm to which the medical instrument is attached. This movement occurs without the robot arm being moved manually. This movement is such that the medical instrument is moved by means of the robot arm in such a way that it treats the living being automatically. Then the control device actuates the robot arm or the relevant robot arm and the medical instrument in such a way that the medical instrument executes the stitching automatically. It should also be mentioned in this connection that the term "control" is to be understood broadly, and should also include regulating in addition to controlling in the narrower sense.

According to one embodiment of the medical work station according to the invention, the latter has an operating console coupled with the control device, which has a mechanical input device coupled with the control device, and in another operating mode generates the signals on the basis of a manual movement of the input device, so that the robot arm executes a movement corresponding to the manual movement. The display device may also be part of the operating console. According to this variant, the robot arm or arms are telemanipulable in the other operating mode by means of the input device, in order to thus treat the living being by means of the medical instrument.

According to one variant of the medical work station according to the invention, the latter has a camera which is intended to create the image of the treatment area of the living being during the treatment. The camera, which is preferably in the form of a 3-D camera, may be in particular attached to the attaching device of another robot arm, in order to be moved to the treatment area in particular by telemanipulation.

The camera may preferably be attached to an endoscope, or integrated into such an instrument. It is then possible to introduce the camera, moved by the other robot arm, into the living being. The images taken by means of the camera can then also possibly be used to monitor the telemanipulated movement of the medical instrument.

In order to better identify the area, the image may be a three-dimensional image. The display device may preferably be set up so that it is able to display a three-dimensional image.

The input device employed may be for example a computer mouse, in particular a 3-D mouse. More complex input devices may also be used as input devices, for example, a so-called pen having a switch to a haptic input device having 6 degrees of freedom, possibly with force, temperature and/or vibration feedback.

According to one embodiment of the medical work station according to the invention, at least one of the manual input devices is of switchable design, so that this input device is usable to identify the area during the operating mode and for telemanipulated movement during the other operating mode.

The medical work station according to the invention may be set up so that various medical instruments are manipulable with it. Possible medical instruments may be intended for example for sticking, stitching, cutting or cauterizing, or for a biopsy or for brachytherapy.

According to one embodiment of the medical work station, the latter may have input means that are intended to select the type of medical instrument. This makes it possible for a treatment of the identified area to be carried out that corresponds to the type selected.

The input means may be based for example on spoken input or on gesture recognition.

In order to enable the control device of the medical work station according to the invention to better plan the automatic movement during the operating mode, the control device may be set up to calculate the movement of the robot arm on the basis of images of the living being taken before the treatment, and/or on the basis of anatomical atlases. The images taken before the treatment may be taken for example by means of an imaging medical technology device, such as for example a magnetic resonance device, an x-ray device or a computer tomograph.

Depending on the embodiment of the medical work station according to the invention, it may for example relieve a surgeon of repetitive, in particular tiring tasks, and thus possibly shorten the duration of the treatment of the living being. To that end autonomous functions may be employed, which are defined "in the image" for example by the surgeon. This may lead on the one hand to a reduction in costs, and on the other hand may result in less of a burden on the living being, for example due to narcosis. To this end, the tasks defined in the image may be performed automatically by the robot or robots. Pre-operative and intra-operative data may be drawn upon.

There may be provision, for example, to first define a task and/or the positions in the image, which is a 2-D, preferably a 3-D image, for example by means of a 3-D mouse, gesture recognition of the input device, a combination with speech input or by means of a more complex input device (e.g., a pen with a switch to a haptic input device having 5 degrees of freedom with force, temperature and vibration feedback), which allow for example a more intuitive selection of regions or areas in the image. The latter allows for example a realization of a virtual 6-D graphic tablet. The input device already present (input device of the operating console) may for example be used (switching between the functions "operating the teleoperator" and "input device for task definition").

The next result may be an automatic movement to points or trajectories, or traversing of areas by the robot or robot arm.

There may be a movement compensation or updating of the scene by a 3-D endoscope, other intraoperative sensor apparatus or a combination of sensors.

Consideration may also be given to (segmented) pre-operative data, or data from anatomical atlases.

The following components may also be integrated into the medical work station according to the invention:
  learning by demonstration,
  collision avoidance with cooperating robots,
  path planning for optimization (optimized for time or force).

BRIEF DESCRIPTION OF THE DRAWINGS

An example of an exemplary embodiment of the invention is depicted in the attached schematic figures. The figures show the following.

DETAILED DESCRIPTION

Figure 1:
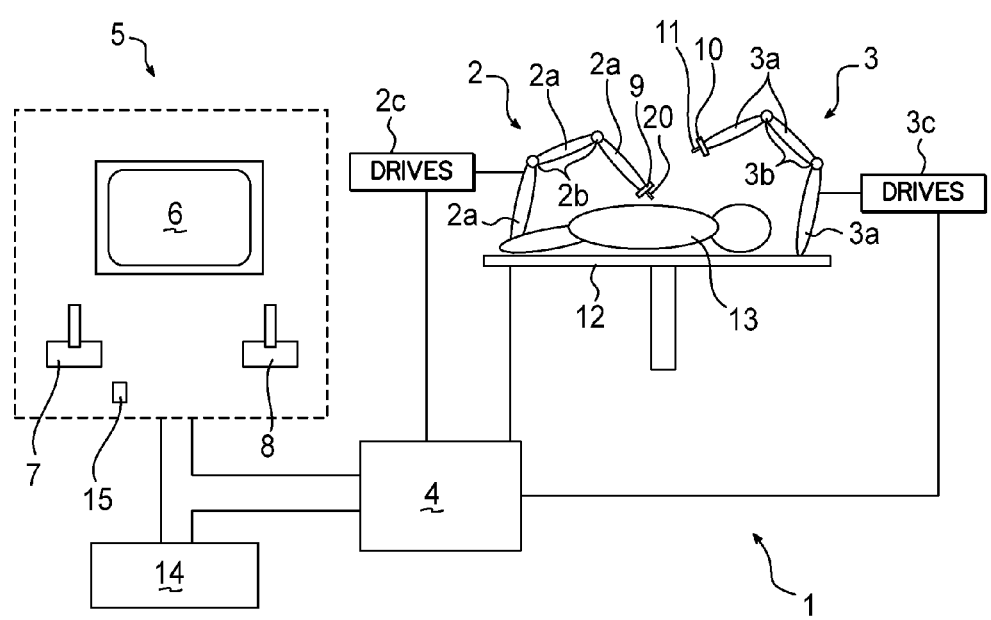
FIG. 1 a medical workstation,
  FIG. 2 a camera guided by means of an endoscope, and
  FIG. 3 a display device of the medical workstation.

FIG. 1 shows a medical work station which has a plurality of robot arms 2, 3, a control device 4, and an operating console 5 coupled with control device 4. Operating console 5 includes a display device 6, which is set up in particular to display three-dimensional images, and manual input devices 7, 8, by means of which a person not shown in greater detail, for example a surgeon, is able to telemanipulate robot arms 2, 3 in a first operating mode, as known in principle to a person skilled in the art.

Figure 2:
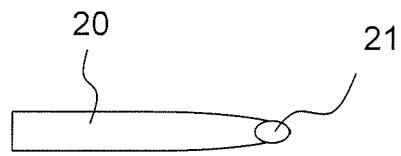

In the case of the present exemplary embodiment, each of the robot arms 2, 3 includes a plurality of members 2a, 3a, which are connected through joints 2b, 3b, and an attaching device 9, 10, to which may be attached for example a medical instrument 11 or an endoscope 20 depicted in greater detail in FIG. 2, into which in particular a camera 21 is integrated. The drives 2c, 3c of robot arms 2, 3, which are in particular electric drives, are connected to control device 4. Control device 4, which is implemented for example as a computer, is set up to activate the drives, in particular by means of a computer program, in such a way that robot arms 2, 3, their attaching devices 9, 10 and thus medical instrument 11 or endoscope 20 execute a desired movement according to a movement defined by means of manual input devices 7, 8. Control device 4 may also be set up in such a way that it regulates the movement of robot arms 2, 3 or of the drives, so that in the present case the term "controls" should also include "regulates."

In the case of the present exemplary embodiment, medical work station 1 is intended so that when it is used, for example a living being 13 lying on a patient table 12 may be treated in particular in a minimally invasive manner by means of medical instrument 11. Medical instrument 11 is for example a scalpel or an apparatus for stitching up tissue of living being 13, and in the first operating mode may be guided into living being 13, telemanipulated by robot arm 3. Medical work station 1 may also include more than two robot arms 2, 3, the one or the additional robot arms likewise being connected to control device 4 and being telemanipulable by means of operating console 5. A medical instrument may also be attached to the additional robot arm.

Medical instrument 11 may be intended for example for sticking, stitching, cutting or cauterizing, or for a biopsy or for brachytherapy.

In the case of the present exemplary embodiment, medical work station 1 may also include a database 14, in particular coupled with control device 4, in which are stored for example pre-operative data from living being 13 and/or anatomical atlases. The pre-operative data include for example pre-operatively recorded image data records assigned to living being 13, which have been registered for example by means of a medical technology device prior to the treatment. Medical technology devices are for example computer tomography devices, magnetic resonance devices, etc. Database 14 may also be coupled with operating console 5, so that for example the pre-operative data and/or the anatomical atlases may be displayed on the display device.

Figure 3:
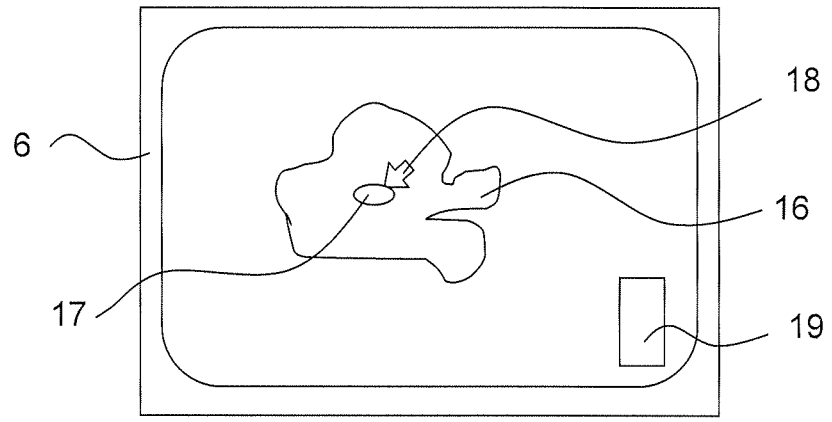

In the case of the present exemplary embodiment, camera 21 is provided in order to display images 16 of the operation situs, i.e., of the area of the living being 13 that is being treated by means of medical work station 1, on display device 6 of operating console 5 during the treatment of living being 13. This camera is connected for example to control device 4, so that image data records recorded by means of camera 21, which are in particular 3-D image records, are displayable as the images 16 on display device 6. One example of an image 16 is shown in FIG. 3.

Camera 21 is attached for example to one end of endoscope 20, or is integrated into that end of endoscope 20. Endoscope 20 is attached by the other end to attaching device 9 of robot arm 2, so that endoscope 20 and thus camera 21 can be moved by means of operating console 5. The person treating living being 13 can thus create suitable images 16 of the operation situs during the treatment, which are depicted on display device 6. The images 16 of the operation situs are in particular three-dimensional images.

In the case of the present exemplary embodiment, console 5 has an input device 15, by means of which the person treating living being 13 can identify an area 17 or a location in the image depicted by means of display device 6. Input device 15 is for example a computer mouse, in particular a 3-D mouse, by means of which a cursor 18 superimposed on image 16 may be moved. Cursor 18 may thus be guided to the particular area 17 by means of input device 15, in order to mark this area 17 for example by clicking. It is also possible to use at least one of the input devices 7, 8 to identify area 17. In this case it may be possible to design the functionality of the relevant input device 7, 8 to be switchable, so that either cursor 18 may be moved or the relevant robot arm 2, 3 may be telemanipulated with the appropriate input device 7, 8.

In the case of the present exemplary embodiment, medical work station 1 can be operated in a second operating mode. For the second operating mode, control device 4 is set up for example in such a way, or a suitable computer program is running on it, so that on the basis of the identified area 17 control device 4 automatically actuates the drives of robot arm 3 to which medical instrument 11 is attached, so that medical instrument 11 automatically treats the area of living being 13 that corresponds to the area identified in image 16. To that end a suitable image processing program for example runs on control device 4, which analyzes image 16 or the area 17 identified in image 16, and then actuates the drives of robot arm 3 so that attaching device 10, to which medical instrument 11 is attached, is moved in such a way that medical instrument 11 is moved to the area of living being 13 that corresponds to the identified area 17. Control device 4 then actuates medical instrument 11 in such a way that the latter carries out a corresponding treatment of living being 13. The calculation of the movement for the relevant robot arm 3 may additionally be made based on the pre-operative data and/or the data of the anatomical atlases. The pre-operative data may for example also be segmented.

It may be possible to provide medical work station 1 with various medical instruments, which are telemanipulated with one of the robot arms 2, 3 in the first operating mode. For the second operating mode, it may be provided that the type of medical instrument used for the automatic treatment of the identified area 17 is manually selectable. To that end, a selection list 19 may be superimposed for example on image 16, which offers a plurality of various medical instruments for selection, one of which may be clicked on by means of cursor 18 in order to be selected. The selection of the medical technology instrument may also be made by means of gesture recognition, spoken input, etc.

The invention claimed is:

1. A medical work station for treating a living being with a medical instrument, the medical work station comprising:
at least one robot arm, said robot arm including a plurality of members interconnected by joints and driven by respective drives for moving said members, said robot arm further including an attaching device for supporting the medical instrument thereon;
at least one control device in communication with said drives of said at least one robot arm, said control device controlling said drives to move said attaching device;
a display device operatively coupled with said control device and displaying at least one image of a treatment area during treatment of the living being; and
an input device operatively coupled with said control device,
wherein said control device has a first operating mode and a second operating mode, wherein when in the first operating mode, said input device is actuable by a user to selectively identify an area of the displayed image corresponding to the treatment area of the living being and said control device automatically calculates movement of said robot arm based on the identified area and actuates said drives to automatically perform a medical procedure in the treatment area of the living being corresponding to the identified area, and when in the second operating mode, said control device is configured to control movement of said robot arm to manual manipulation of said input device by a user such that movement of said robot arm corresponds to manual movement of said input device.

2. The medical work station of claim 1, wherein said operating console comprises said display device.

3. The medical work station of claim 1, further comprising:
a second robot arm including a plurality of members interconnected by joints and driven by respective drives for moving said members, said second robot arm further including an attaching device;
a camera operatively coupled to said attaching device of said second robot arm;
said camera generating said image of the treatment area of the living being during treatment thereof.

4. The medical work station of claim 3, further comprising:
an endoscope operatively coupled to said attachment device of said second robot arm; said camera being supported on said endoscope.

5. The medical work station of claim 1, wherein:
said image displayed by said display device is a three-dimensional image.

6. The medical work station of claim 1, wherein said input device is a computer mouse.

7. The medical work station of claim 6, wherein said computer mouse is a three-dimensional computer mouse.

8. The medical work station of claim 1, further comprising input means configured to be actuable by a user to select one of a plurality of available medical instruments for use by said robot arm or wherein said input device is further actuable by a user to select one of a plurality of available medical instruments for use by said robot arm.

9. The medical work station of claim 8, wherein said control device responds to at least one of a spoken input or a recognized gesture to select the medical instrument.

10. The medical work station of claim 1, wherein said robot arm is adapted to automatically perform at least one of sticking, stitching, cutting or cauterizing, biopsy, or brachytherapy procedures in said first operating mode of said control device.

11. The medical work station of claim 1, wherein said control device calculates movement of said robot arm based on at least one of:
a) images of the living being obtained prior to the treatment; or
b) anatomical atlases.

* * * * *